United States Patent
Madhavamenon et al.

(10) Patent No.: US 9,861,610 B2
(45) Date of Patent: Jan. 9, 2018

(54) PROCESS FOR SELECTIVE EXTRACTION OF BIOACTIVE AND BIOAVAILABLE CINNAMON POLYPHENOLS AND PROCYANIDIN OLIGOMERS AND A STABLE COMPOSITION THEREOF

(75) Inventors: Krishnakumar Illathu Madhavamenon, Kerala (IN); Abin Isaac, Kerala (IN); Dineshkumar Unnikrishnan, Kerala (IN); Aswin Koshy Jacob Vaidyan, Kerala (IN); Balu Paulose Maliakel, Kerala (IN)

(73) Assignee: AKAY FLAVOURS & AROMATICS PVT LTD., Kerala (IN)

( * ) Notice: Subject to any disclaimer, the term of this patent is extended or adjusted under 35 U.S.C. 154(b) by 1120 days.

(21) Appl. No.: 13/562,337

(22) Filed: Jul. 31, 2012

(65) Prior Publication Data

US 2013/0035380 A1 Feb. 7, 2013

(30) Foreign Application Priority Data

Aug. 1, 2011 (IN) .......................... 2239/CHE/2010

(51) Int. Cl.
*A61K 31/353* (2006.01)
*C07D 493/18* (2006.01)
*A23L 33/105* (2016.01)

(52) U.S. Cl.
CPC .......... *A61K 31/353* (2013.01); *A23L 33/105* (2016.08); *C07D 493/18* (2013.01)

(58) Field of Classification Search
CPC .................................................. C07D 493/18
(Continued)

(56) References Cited

U.S. PATENT DOCUMENTS 6,200,569 B1 3/2001 Cheng
7,174,000 B2 2/2007 Fehre
(Continued)

OTHER PUBLICATIONS

Yanagida et al. Separation of proanthocyanidins by degree of polymerization by means of size-exclusion chromatography and related techniques. J. Biochem. Biophys. Methods 56, 311-322 (2003).*

(Continued)

*Primary Examiner* — Jeffrey S Lundgren
*Assistant Examiner* — Sara E Townsley
(74) *Attorney, Agent, or Firm* — Mark M. Friedman (57) ABSTRACT

The present invention relates to a process for selective extraction of bioactive and bioavailable cinnamon polyphenols and procyanidin oligomers of the type A and type B, of more than 90% purity as gallic acid equivalent which comprises the steps of removing the organic solvent from the extract to produce the free flowing oleoresin and drying of the residue under optimized conditions to produce a polyphenol and procyanidin Type A & B polymer rich solid which on subsequent extraction with water or with mixture of water and acetone or water and lower alcohol and further evaporation to a solid content of not more than 6% and subsequent chromatographic separation to obtain fractions containing procyanidin type A and B polymers free of coumarins and cinnamaldehyde. The present invention also relates to stable composition comprising cinnamon polyphenol rich powder for delivering maximum bioactivity upon oral administration.

22 Claims, 11 Drawing Sheets

Representative chemical structure of a procyanidin oligomer with Type A & B linkages.

(58) Field of Classification Search
USPC .......................................................... 514/456
See application file for complete search history.

(56) References Cited

U.S. PATENT DOCUMENTS

| | | | |
|---|---|---|---|
| 7,504,118 | B2 | 3/2009 | Miller |
| 2001/0039923 | A1 | 11/2001 | Yamamuka et al. |
| 2005/0164956 | A1 | 7/2005 | Schmitz |
| 2006/0013903 | A1 | 1/2006 | Romero |
| 2006/0073220 | A1 | 4/2006 | Daugherty |
| 2006/0275515 | A1 | 12/2006 | Ovadia |
| 2007/0292540 | A1 | 12/2007 | Gow |
| 2008/0306141 | A1 | 12/2008 | Glinski |
| 2010/0029756 | A1 | 2/2010 | Tempesta |

OTHER PUBLICATIONS

Nonaka et al. Tannins and Related Compounds. Part 13. Isolation and Structures of Trimeric, Tetrameric, and Pentameric Proanthicyanidins from Cinnamon. J. Chem. Soc. Perkin Trans. 1, pp. 2139-2145 (1983).*

Woehrlin et al., "Quanitification of Flavoring Constituents in Cinnamon: High Variation of Coumarin in Cassia Bark from the German Retail market and in Authentic Samples from Indonesia", J. Agric. Food Chem., 2010, 58, pp. 10568-10575.

Peterson et al., "Cinnamon Extract Inhibits Tau Aggregation Associated With Alzheimer's Disease In Vitro", Journal of Alzheimer's Disease, 17 (2009), pp. 585-597.

"High Daily Intakes of Cinnamon: Health Risk Cannot Be Ruled Out", BFR Health Assessment No., 044/2006, Aug. 18, 2006, pp. 1-15.

Anderson et al., "Isolation and Characterization of Polyphenol Type-A Polymers from Cinnamon with Insulin-like Biological Activity", J. Agric. Food Chem., 2004, 52 pp. 65-70, Nov. 3, 2015.

Kanuri et al., "Cinnamon and its Medicinal Benefits", Dept. of Nutritional Medicine, University of Hohenheim, Stuttgart, Germany, Apr. 23, 2009.

Lu et al., "Hypoglycemic Activities of A- and B-type Procyanidin Oligomer-righ Extracts From Different Cinnamon Barks", Phytomedicine 18 (2011), pp. 298-302.

Singleton et al., "Colorimetry of Total Phenolics With Phosphomolybdic-Phosphotungstic Acid Reagents", Dept. of Viticulture and Enology, University of California, Davis, CA, USA, Phenolics Determination,pp. 144-158.

G. Kanuri and I. Bergheim, Cinnamon and its medicinal benefits, Published Online Apr. 23, 2009 http://herbication.com/5.htm.

* cited by examiner

Figure 1: Representative chemical structure of a procyanidin oligomer with Type A & B linkages.

Figure 2: HPLC profile of crude polyphenolic extract at 20% polyphenol content level.

Figure 3: HPLC profile of de-coumarinated polyphenolic extract with 90% polyphenol content.

Figure 4: HPLC profile of purified procyanidin A-type trimer (Molecular weight 863.4).

Figure 5: HPLC profile of purified procyanidin B-type dimer (Molecular weight 577.6)

FIG. 10

US 9,861,610 B2

PROCESS FOR SELECTIVE EXTRACTION OF BIOACTIVE AND BIOAVAILABLE CINNAMON POLYPHENOLS AND PROCYANIDIN OLIGOMERS AND A STABLE COMPOSITION THEREOF

FIELD OF INVENTION

The present invention is a method for the extraction, purification and concentration of polyphenols enriched with the bioactive procyanidin oligomers from the barks of various *cinnamomum* species including, but not limited to *cinnamomum verum/cinnamomum Zeylanicum, cinnamomum cassia/cinnamomum aromatica, cinnamomum burmanii* and *cinnamomum tamala* by selectively eliminating the toxic coumarins that may be present in the raw material in various degrees. The isolated coumarin free polyphenols were formulated to minimum 75% gallic acid equivalent purity level and were water soluble free flowing powders capable of easy incorporation into food and beverages and easily compressible into tablets and capsules. Isolated polyphenols were also formulated into various degrees of polyphenol contents (UV spectrophotometry) and type A & B procyanidin content (High Performance Liquid Chromatography, HPLC & Liquid Chromatography/mass spectrometry, LC/MS/MS) and subjected to an antidiabetic study on streptozotocin induced diabetic wistar rats to check the bioactivity of the isolated polyphenols, to delineate efficacy with polyphenol and/or procyanidin content. It is observed that the efficacy is proportional to the polyphenol and/or procyanidin content and the formulated polyphenol with 75% gallic acid equivalent purity and minimum 8% procyanidin type A polymer content was found to offer the maximum health benefits as compared to the prior art results on aqueous extract of *cinnamon zeylanicum* or *cinnamomum cassia*. Isolated polyphenols in the highest purity level was also found to be safe upon to toxicity studies and are not genotoxic.

BACKGROUND OF THE INVENTION

Bio-polyphenols are super active substances, and can add a great deal to nutritional needs in health and disease. Their significant contribution towards health include antioxidative, antimicrobial, and possibly antidiabetic, anti-carcinogenic, and/or cardioprotective effects.

*Cinnamomum* spp, (cinnamon/cassia) contains essential oils, catechins, procyanidins, coumarins, tanning agents, phenolic carboxylic acids, lignans and mucins, in which coumarin is reported to be moderately toxic to liver and kidney (Giridhar Kanuri and Bergheim, Cinnamon and its medicinal effects, published online Apr. 23, 2009). Higher concentrations of coumarins can be measured particularly in certain types of cinnamon/cassia. Many extracts of cinnamon/cassia obtained in capsules were found to contain coumarins in high levels, (The Federal Institute for Risk Assessment, BfR Health Assessment No. 044/2006, 2006). As coumarins are generally soluble in alcohol, hydro-alcoholic extracts and alcoholic extracts may contain higher levels. The coumarin levels were found to be varying within various species of cinnamon and even different at barks collected from various parts within a tree ((Friederike W et. al., Journal of Agricultural and Food Chemistry, 2010, 58(19) pp. 10568-10575). This is a major concern in making use of the valuable cinnamon/cassia extracts as Nutraceutical/dietary supplement or food ingredient. Besides the high coumarin levels, the cinnamaldehyde levels in cinnamon powder capsules may possibly constitute a risk for pregnant women. Animal experiment studies indicate that taking cinnamaldehyde during pregnancy could lead to damage to the foetus (The Federal Institute for Risk Assessment, BfR Health Assessment No. 044/2006, 2006).

Recent research has mostly explored the benefits of cinnamon/cassia in blood-sugar management. In a study, Anderson et al (*Journal of Agricultural and Food Chemistry*, 2004, 52, pp. 65-70), isolated insulin action-enhancing complexes from the aqueous extracts of cassia/cinnamon and then characterized by nuclear magnetic resonance and mass spectroscopy as polymers composed of catechin/epicatechin with a molecular mass of 288, trimers with a molecular mass of 864 and tetramer with a mass of 1152. Their protonated molecular masses indicated that they are A type doubly linked procyanidin oligomers of the catechins and/or epicatechins. These polyphenolic polymers found in cinnamon/cassia may function as antioxidants, potentiate insulin action rendering cells more sensitive to insulin, and may be beneficial in the control of glucose intolerance and diabetes.

In another study an aqueous extract of cinnamon was reported to be effective in segregating the Alzheimer's disease causing proteins in vitro. (Peterson et al, *Journal of Alzheimer's Disease*, 2009, 17, 585).

In a recent study (Lu Z et. al, Phytomedicine, 2011, 18 (4), pp 298-302) the presence of both Type A and Type B procynidin polymers were established in various *cinnamomum* species and were shown to be bioactive.

Despite the health benefits of cinnamon/cassia polyphenols and procyanidins, no cost effective and commercially viable processing methods are available to selectively isolate coumarin free active polyphenols containing definite percentage of procyanidins, in sufficient purity, for nutraceutical, cosmeceutical and functional food ingredient applications.

Though the prior arts, U.S. Pat. No. 6,200,569 B1, US 2006/0013361 A1, US 2006/0013903 A1, and US 2009/7504118 B2 have detailed the isolation and various uses of cinnamon/cassia extracts containing procyanidins, such as for reduction of blood glucose and/or glycosylated hemoglobin levels, as a weight loss ingredient by reducing body fat and/or as a blood glucose lowering ingredient, to enhance creatine transport to muscles and for oral administration to control the blood glucose as well as improving glucose tolerance respectively, all these patents describe a highly temperature-time sensitive aqueous extraction protocol involving 50 to 200 times water. Though the method has been successfully applied to 1 to 50 g raw material, its commercial scale applicability has been seriously limited by various factors of the process such as the requirement of huge quantity of water and subsequent handling issues imparted by the mucilaginousin cinnamon/cassia bark, time-temperature sensitivity of the process and subsequent gel filtration using expensive adsorbents like Sephadex LH-20 and final concentration to powder. In addition no information has been given about the procyanidin content, polyphenol content, coumarin content, and organoleptic properties of the resulting extracts.

In another art US 2006/0073220 A1, an adsorbent resin based purification process for polyphenols and proanthocyanidins from various fruits and plant materials including cinnamon, using polystyrene copolymers containing electron withdrawing groups like bromine and non-substituted resins were detailed. Though high purity isolation of polyphenols and procyanidin polymers were claimed, no information has been given with respect to the polyphenol recovery from cinnamon, toxic and allergic coumarin and cinnamldehyde levels in the isolated polyphenols, and relative percentages of type A & B polymers that can be isolated from *cinnamomum* species. Though it is a general method of isolation of polyphenols from various natural raw materials, no informations have been given in the context of polyphenols or procyanidin type A & B polymers from *Cinnamomum* spp and their effect upon bioactivity.

In another US patent 2006 0275515 A1, a method of preparation of a cinnamon extract with antiviral properties against enveloped viruses including influenza A, parainfluenza and HSV-1 were mentioned. However no informations regarding the active molecules or procyanidin molecules or polyphenol content has been mentioned.

In another prior art US 2007/0292540/A1, the invention was fractionation of various chemical constituents in cinnamon. Supercritical carbon dioxide extraction of aroma fraction of cinnamon followed by aqueous extraction of the residue to obtain a polyphenolic acid and polysaccharide rich fraction were reported. The polyphenolic acid fraction was then passed through Sephadex LH 20 adsorbent resin to separate tannin phenolics from non-tannin phenolics. The disadvantage of this method is that it does not specify coumarin levels in various fractions, and does not provide any quantification and characterization of procyanidin levels in the final extract. Another limitation of this method is that it employs relatively expensive supercritical extraction method for the removal of the aroma compounds and expensive Sephadex LH 20 for the purification of polyphenols.

In a recent art US 2008/0306141 A1, procyanidin A-type polymer enriched extract was isolated from cinnamon bark using an organic solvent like acetone for extraction. Though this method can be used for bulk extraction, the percentage purity of the final product such as polyphenol content, or procyanidin Type A content etc is not assured. Another limitation of this method is that there is no plausible elimination of toxic coumarins from the procyanidin extract. It is also not possible to recover the aroma fraction of cinnamon bark, a valuable food flavourant. The method also does not confirm the purity of the procyanidins or the identity of the product as type A procyanidins. The prior art only mentions that the analysis was based on HPLC measurements.

In another prior art US 2010 0029756 A1, a method for the selective isolation of procyanidin type A tetramer with a molecular formula of $C_{60}H_{48}O_{24}$ has been mentioned and its plausible applications as anti-inflammatory, anti microbial and bactericidal uses were speculated. The invention employed expensive instrumental techniques like multilevel preparative chromatographic instruments for the isolation and purification of the molecule. Further, no attempt have been mentioned to establish the level of bioactivity of the said molecule.

In another prior art US 2011/0039923 A1, the invention describes a process for the isolation of pentameric procyanidin rich cinnamon extract for antiviral applications. The disadvantage of the prior art is that it does not mention about the recovery of bioactive Type B polymers from cinnamon. Moreover, no information about the efficacy in relation with polyphenolic/procyanidin content has been furnished. In the present invention we describe a process for the isolation of total procyanidins including Type A and Type B polymers by eliminating the toxic coumarins and cinnamaldehyde.

The present invention attempts to overcome the hurdles in all these prior arts. In the present method, an easily scalable protocol is used to process cinnamon/cassia powder of the order of tones, using a 3 to 5 fold excess of water-based solvent for the isolation of polyphenols without coumarins.

An advantage of the present invention is an extraction method in which there is complete fractionation of cinnamon bark into a flavour ingredient and polyphenol powder can be achieved. The polyphenol powder was shown to be more than 90% pure (gallic acid equivalent) with procyanidins type A & B polymers, in which type A is present in 5 to 20% and type B polymer in 0.5 to 5%. Type A polymer was shown to be a mixture of doubly linked catechinlepicatechin trimer, tetramer, pentamer whereas Type B is a dimer formed by the B-type links.

Another advantage of the present invention is that it helps to selectively eliminate the toxic coumarins naturally present in many *cinnamomum* species and also helps to eliminate the other toxic or allergen components such as cinnamaldehye which is associated with the oil of cinnamon bark.

The present invention also delineate the level of polyphenol/procyanidin content with the bioactivity, as exemplified by the blood sugar levels, lipid levels and liver function markers. It is found that the bioactivity is directly proportional to the polyphenol/procyanidin content of the extract. As the polyphenol content increases from 15 to 75%, the blood sugar management potential was found to have a three-fold increase and the insulin potency increases 2.6 fold. The study also proved that coumarin and cinnamaldehyde contribution towards bioactivity is negligible as compared to the polyphenol content.

This invention can also be used for the direct extraction of polyphenols from cinnamon bark powder using water or alcohol or acetone or mixtures thereof and purification employing adsorbent chromatography.

The present invention also has the advantage that it can be easily scaled up to process tones of raw materials cost effectively. The invention also provides a unique method for the production of lower oligomers of polyphenols which are water soluble and more bioavailable.

The present invention also provides total isolation of polyphenols from cinnamon bark with an yield corresponding to greater than 90% recovery.

Another advantage of the method is to provide a process for the production of polyphenol isolates with high antioxidative index, ORAC value (Oxygen Radical Absorbing Capacity), not less than 3000 μmol Trolox equvalent/g.

Another advantage of the process is to derive a bioactive coumarin-free polyphenols in water soluble powder form as proved by the efficacy to control the blood sugar levels in streptozotocin induced diabetic rats.

Another advantage of the process is to optimize the polyphenol levels and procyanidin Type A & B levels for maximum bioactivity, as shown by the blood-sugar management study in streptozotocin induced diabetic rats Another advantage of the present study is to provide safe and non toxic coumarin free bioactive polyphenols capable of reducing the LDL and, triglyceride levels in diabetic rats.

Another advantage of the present study is to provide a cinnamon bark extracted coumarin free polyphenols for maintaining the liver health of diabetic rats as monitored by the liver function markers alanine transaminase (ALT) and alakaline phosphatase (ALP).

Yet another advantage is the stable, directly compressible and non hygroscopic form of the polyphenolic extract for easy handling and formulation in tablet and capsule forms Object of the Invention An object of the present invention is to propose a new method for the isolation of polyphenols enriched with procyanidins (Type A and B polymers) from dried barks of various *cinnamomum* species.

Another object of the present invention is to propose a process for the isolation of polyphenols from various *cinnamomum* species with more than 90% purity and containing the procyanidin A type polymers within a range of 5-20% and procyanidin B type polymers within a range of 0.5-5% as characterized by LC/MS.

Another object of the present formulation is to develop a water soluble and stable polyphenol isolate in free flowing, easily compressible powder form with not less than 75% total polyphenol content and not less than 8% procynidin Type A and 0.5% Type B polymer, which can be used as functional food ingredient, nutraceutical and/or cosmeceutical ingredient.

Another object is to develop an extraction and purification protocol to selectively extract polyphenols and procyanidins from various *cinnamomum* species containing various levels of toxic coumarins.

Still another object is to develop a polyphenol concentrate by selectively eliminating the toxic coumarins present in the raw material, in a range not more than 100 ppm as quantified by HPLC.

Yet another object is to develop an extraction and purification protocol to selectively extract polyphenols and procyanidins from various *cinnamomum* species eliminating cinnamaldehyde in the raw material in a range not more than 100 ppm as quantified by HPLC.

Still another object is to propose a method which can be used to produce organic polyphenols and procyanidins with greater than 90% purity, using water and ethanol alone.

Another object is to extract total polyphenols from cinnamon bark powder with minimum 90% recovery.

Yet another object of the present invention is to prepare a deflavoured polyphenol concentrate for various applications by selectively removing the strong aroma giving essential oils, terpenoids and cinnamaldehyde, which limits its application in the above mentioned fields.

Another object is to provide a unique method for the production of water soluble polyphenols and procyanidins (lower oligomers) which are more bioavailable.

Another object of the present invention is to provide a method for the isolation and separation of higher procyanidin oligmers, (hexamer to higher analogues) from cinnamon barks which are less water soluble than the lower oligomers.

Another object is to derive a cinnamon/cassia (oleoresins) flavour, as a byproduct of the polyphenol isolation process, using solvent extraction or supercritical extraction for use in food/beverage applications.

A further object of the present invention is to isolate a polyphenol concentrate from various *cinnamomum* species which is having an antioxidant property as seen from ORAC value (oxygen radical absorbance capacity) measurements.

Yet another object of the present invention is to provide a complete fractionation of cinnamon/cassia barks to derive a food grade natural flavour product and a value added standardized procyanidin rich functional food ingredient for nutraceutical/dietary supplement/functional food ingredient/cosmeceutical applications, as characterized by high antioxidant index.

Still another object is to provide a process which is easily scalable to any scale, or to process even tones of raw materials for polyphenol extraction.

Yet another object of the present invention is to prove bioactivity and safety of the isolated coumarin-free polyphenols as proved by the blood-sugar management efficacy on diabetic rats Yet another object of the present invention is to investigate the effect of polyphenol/procyanidin polymer concentration on the bioactivity and to provide a formulation with the best stability, solubility and an optimum concentration of polyphenol/procyanidin content for the maximum bioactivity and efficacy.

Further objects and advantages of this invention will be more apparent from the ensuing description.

BRIEF DESCRIPTION OF DRAWINGS

FIG. 6 (A and B): LC/MS profile of purified procyanidin extract (Zoomed view from m/z 500 to 1000 and 1000 to 2000), showing various Type A & B procyanidin oligomers.

FIG. 7 (A-C): Effect of extracts of 20% (Group-I), 45% (Group-II) and 75% (Group-Ill) polyphenol content respectively on the fasting and post pradianal blood glucose levels of diabetic wistar albino rats.

DESCRIPTION OF THE INVENTION

Figure 1:
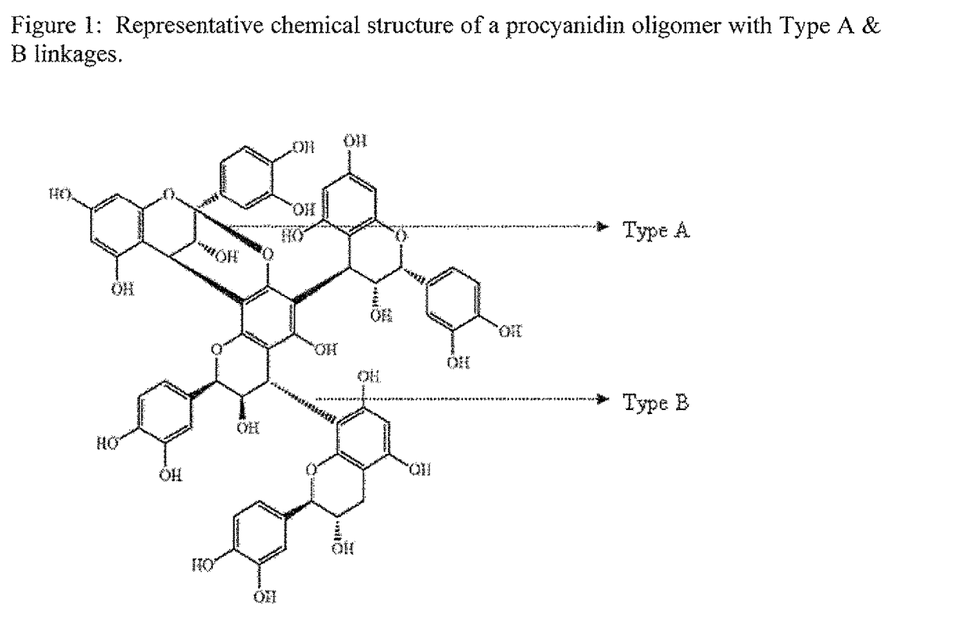
FIG. 1: Representative chemical structure of a procyanidin oligomer with Type A & B linkages.
Figure 2:
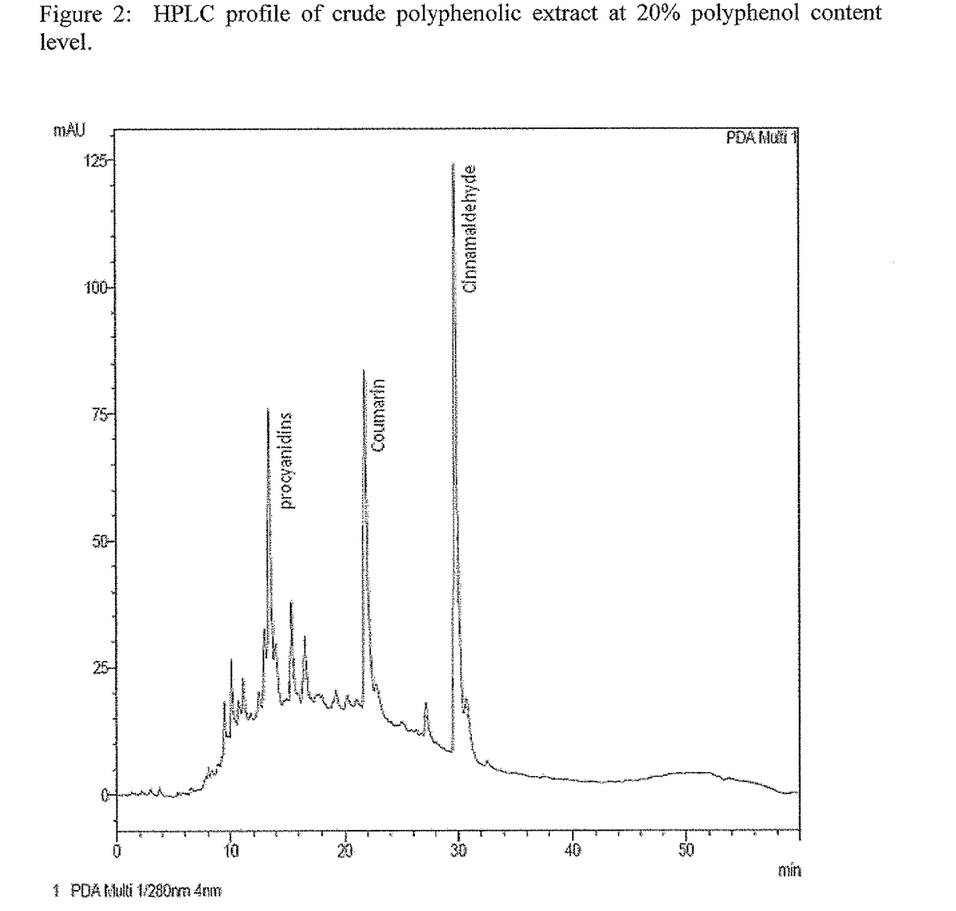
FIG. 2: HPLC profile of crude polyphenolic extract at 20% polyphenol content level.
Figure 3:
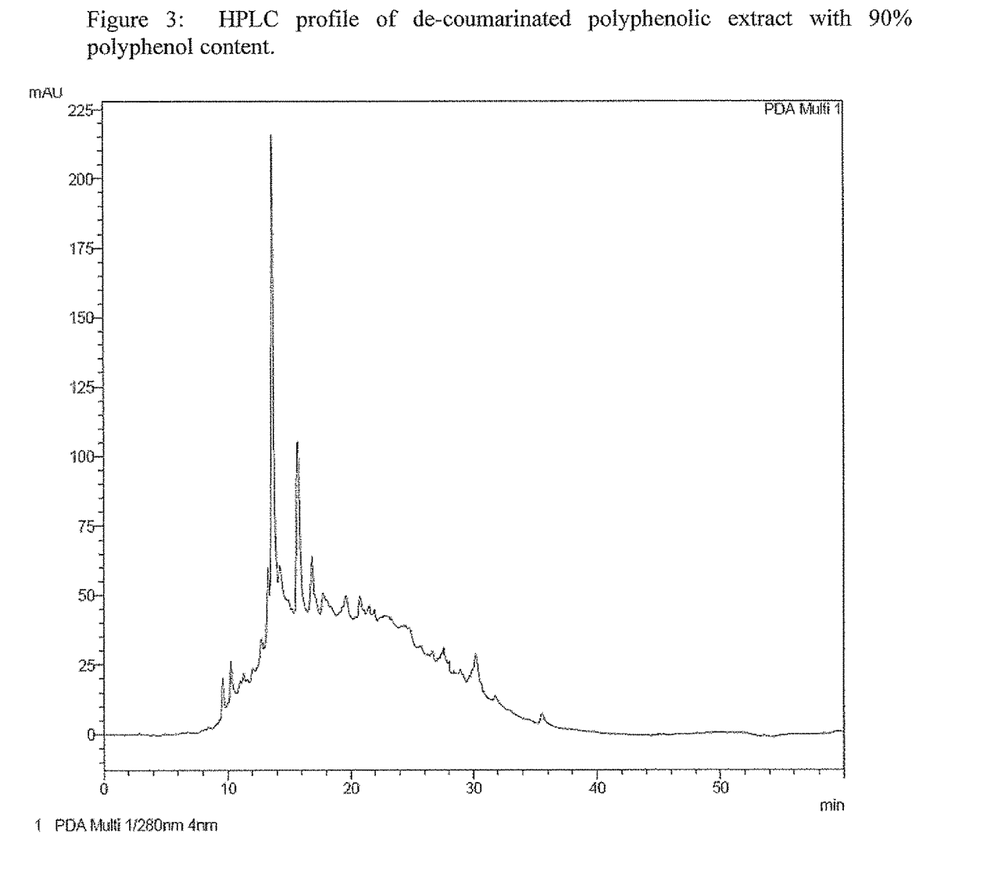
FIG. 3: HPLC profile of de-coumarinated polyphenolic extract with 90% polyphenol content.
Figure 4:
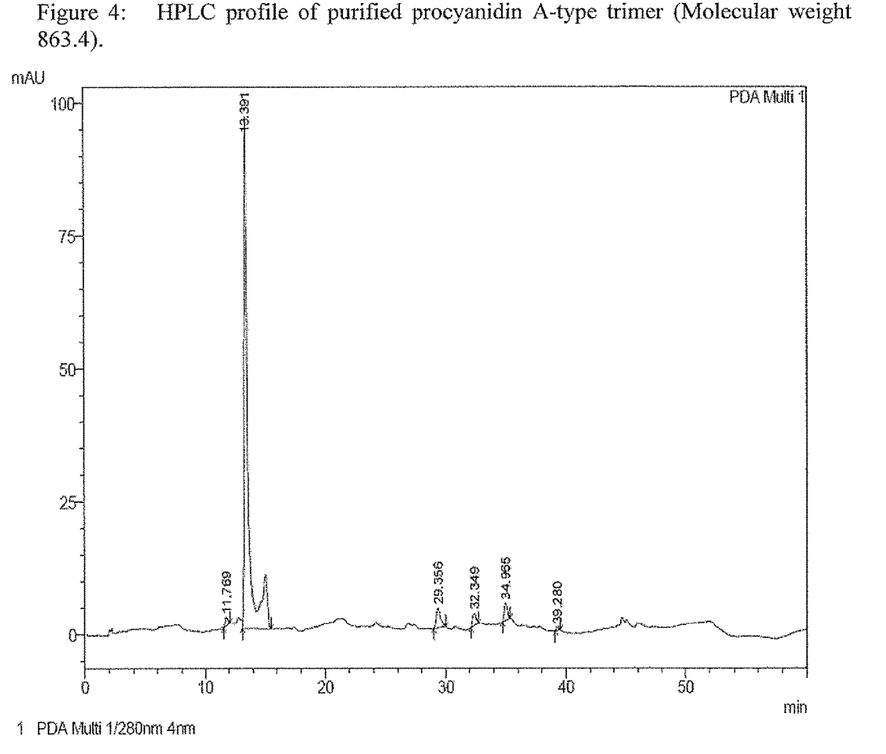
FIG. 4: HPLC profile of purified procyanidin A-type trimer (Molecular weight 863.4).
Figure 5:
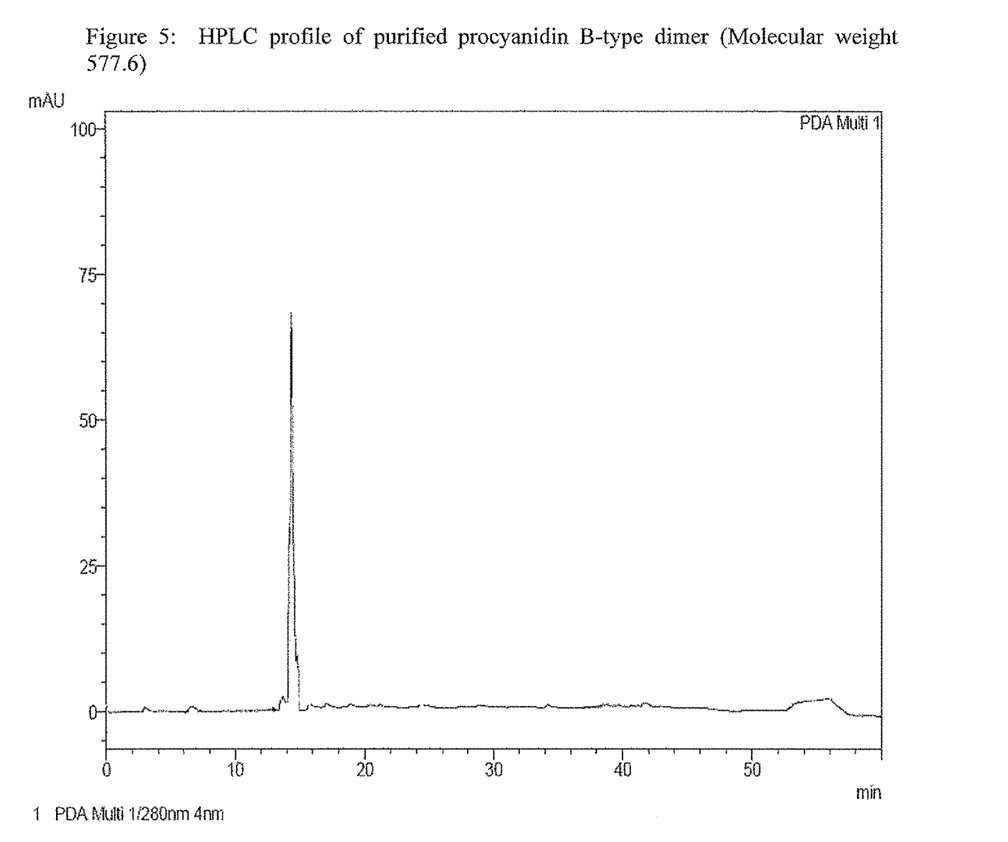
FIG. 5: HPLC profile of purified procyanidin B-type dimer (Molecular weight 577.6)
Figure 6A:
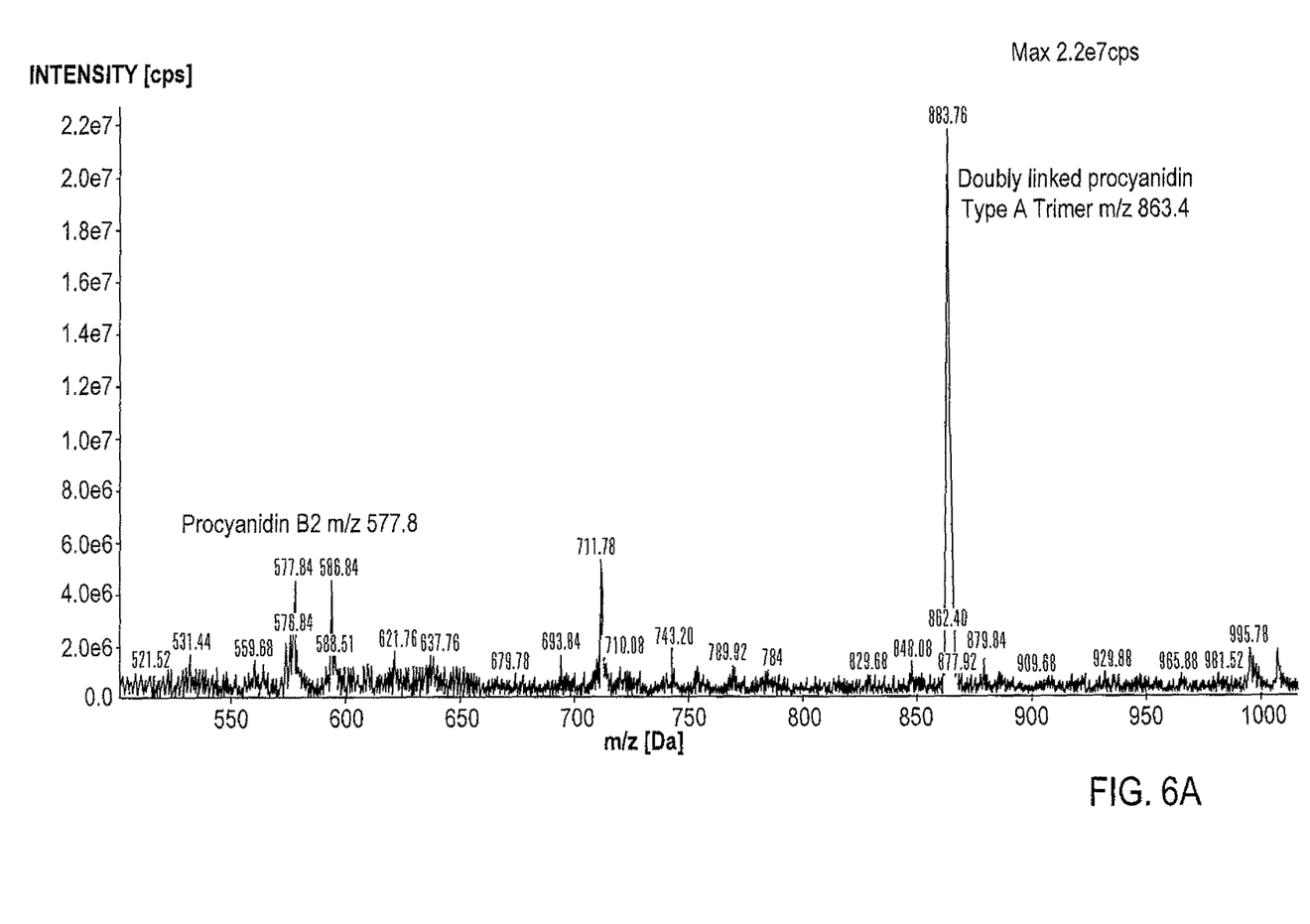
Figure 6B:
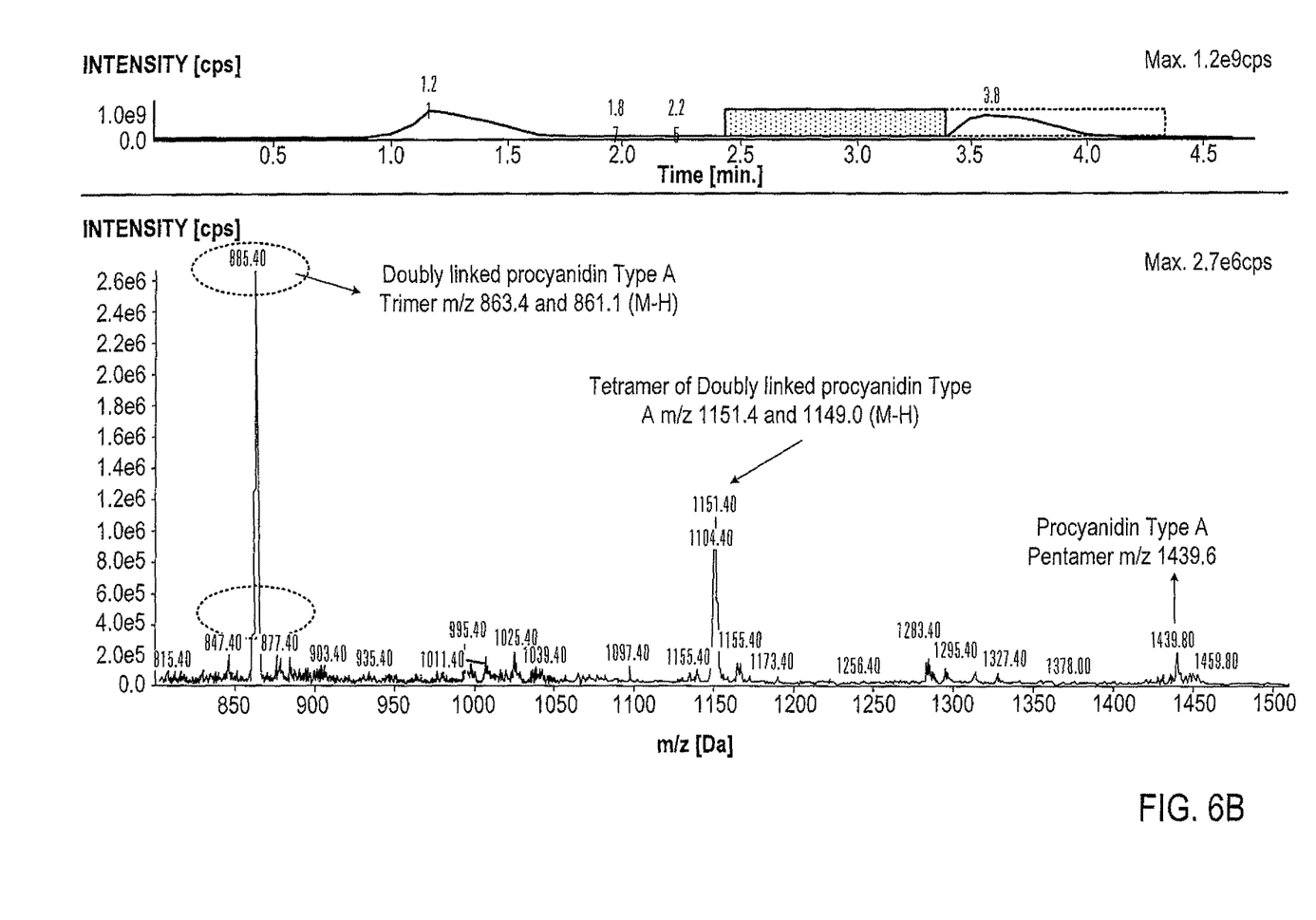

According to this invention a novel method has been developed which allows the selective extraction of bioactive and bioavailable polyphenols and procyanidin oligomers both type A and Type B, from various *cinnamomum* species, with more than 90% purity and recovery by eliminating the toxic coumarins, cinnamaldehyde etc to not more than 100 ppm levels, using non toxic solvents. The process can also be carried out to produce organic quality polyphenols using only water and ethanol. Lower aliphatic ketones containing less than 5 numbers of carbon atoms, lower aliphatic alcohols containing less than 5 numbers of carbon atoms and/or water alone can also be used for the process. When water alone is used, the extraction needs to be carried out at a temperature ranging from 50 to 90° C. at acidic pH at 4 to 5.5. The product obtained in water soluble, free flowing and directly compressible form was found to contain not less than 90% polyphenol content as Gallic acid equivalent. Polyphenol content was estimated with Folin-Ciocaltue method as Gallic acid equivalent (Singleton V. L and Rossi J. A. American Journal of Ecology and Viticulture, 1965, 16, pp. 144-158) and Procyanidin type A polymers was within a range of 5-20% and procyanidin B type polymers within a range of 0.5-5% eliminating coumarins and cinnamaldehyde in a range not more than 100 ppm. Procyanidin type A and procyanidin B type polymers are different groups of polyphenol polymers with difference in type of linkages. General chemical structure comprises linear chains of flavan-3-ols linked together through C(4)-C(8) bonds to form Type B bonds and by an ether linkage between C(2) and C(4) of the successive units and the oxygen at the C(7) position and C(6) or C(8) positions of the lower unit to form type A linkages (FIG. 1). Though these are not separately extracted, the properties of this group A and B in a range of 5-20% and 0.5-5% respectively, together exhibit higher potency, stability, anti-cholesterol property and obesity controlling factor. Procyanidin content was measured on a HPLC instrument fitted with a reverse phase C18 column using mobile phase containing solvent (A) water containing 0.2% acetic acid and (B) 95% methanol containing 0.2% acetic acid under a linear gradient 0-40% B in 45 minutes. The purified procyanidin A type trimer, tetramer and B type dimer were purified from cinnamon extract employing gel permeation chromatography using Sephadex LH20 followed by preparative HPLC as described in an earlier US Patent 2005/0164956 A1. Confirmation of identity of the procyanidin peaks were done by LC/MS technique. The product was showing high antioxidant capacity as evident from ORAC, FRAP, TEAC measurements. The isolated polyphenols has been subjected to anti-diabetic study on streptozotocin induced diabetic rats to delineate the effect of polyphenol content on bioactivity.

Dried cinnamon/cassia is coarse ground and flaked to 1 to 25 mm pieces, and charged into a stainless steel vessel with a steam jacketing condenser and solvent dispensing lines. A mixture of hexane and acetone, most preferably 60 to 90% v/v of hexane is pumped into vessel in a range of 1:3 to 1:5 w/v and circulated for 2 hours at 20 to 50° C. The solvent is filtered, hereafter termed as miscella, and stored in a separate tank. The extraction is repeated two more times and the miscella obtained at each is mixed together. It is then evaporated under reduced pressure to contain less than 25 ppm solvent residue. The free flowing dark brown liquid called oleoresin thus obtained will have the strong characteristic aroma of cinnamon/cassia which can be used as a food flavour ingredient.

The waste obtained after hexane/acetone extraction contains 5 to 20% of organic solvent imbibed into the waste which will hamper further extraction of polyphenol. The imbibed solvent is then removed by heating under vacuum at a temperature of less than 50° C. to remove the imbibed solvent to less than 5% level without damaging the active polyphenol content in cinnamon matrix. The residue is then extracted with acetone and water or ethanol and water preferably 30% to 60% v/v organic solvent for 3 times, at a temperature not exceeding 50° C. with circulation. The miscella is filtered and evaporated under vacuum at 40°-50° C. to a total dissolved solid level of 5 to 20%. The extract is allowed to settle at low temperature, preferably below 20° C. for 6 to 12 hours and filtered. The solid mass thus obtained is insoluble in water and contains higher molecular weight oligomers of procyanidins. The filtrate is loaded onto an adsorbent divinyl benzene-crosslinked polystyrene resincolumn and washed repeatedly with water at 25° C. to 30° C. and then with hot water at 40-50° C. and further with water containing 1 to 3% ethanol. After the washings, column is eluted with ethanol alone or ethanol and water mixture, most preferably 70 to 95% ethanol v/v. Methanol and Isopropanol can also be used for eluting the polyphenols from adsorbent column. The column eluent is collected, evaporated under vacuum or most preferably spray dried to get free flowing polyphenol rich powder containing procyanidin type A and B polymers free of coumarins and cinnamaldehyde.

Detailed in vivo study has undertaken on normal and streptozotocin induced adult diabetic rats of Wister strain (180-200 g body weight) to assess the effect of *cinnamomum* polyphenol isolates of various levels on blood sugar management, on other hematological parameters and histopathological examinations of organs. Animal experiments were designed and conducted in strict accordance with the ethical norms approved by the Institutional Animal Ethics Committee falling in line with the CPCSEA guidelines. Animals were rendered diabetic by a single intraperitoneal injection of Streptozotocin (40 mg/Kg BWt) which was dissolved in freshly prepared cold sodium citrate buffer at a $p^H$ of 7.4. The animals were closely monitored and their blood glucose level was checked at constant intervals using a blood glucose meter. After a week, those animals whose fasting blood glucose level was more than 250 mg/dl were considered diabetic and selected for the detailed study. The animals were randomly placed in five different groups A,B,C,D & E, each group with six animals. The first three groups (I, II, & III) were provided with the decoumarinated extracts of *cinnamomum cassia* containing less than 100 ppm of coumarin and less than 100 ppm of cinnamaldehyde and polphenols 20, 45 and 75% respectively. 20% polyphenol content extract was found to contain not less than 3% procyanidin Type A polymer and 0.3% type B polymer (Extract A, Group I); 45% polyphenol content extract was found to contain not less than 5% procyanidin Type A polymer and 0.5% type B polymer (Extract B, Group II); and 75% polyphenol extract was found to contain not less than 8% procyanidin Type A polymer and 0.5% type B polymer (Extract C, Group III). The fourth group, D, was a positive control with Glibenclamide, and fifth group, E, was the negative control, treated with only carboxymethylcellulose. The drugs and extracts were administered by oral gavage in the morning. Glucose tolerance test (GTT) was carried out on the 1st, 15th and 30th day of the study. Animals were fasted overnight and fasting blood glucose (FBG1) was checked. After half an hour of extract treatment FBG2 was checked followed by glucose administration (2 mL of 20% glucose solution as oral gavage). The blood glucose levels were monitored after 30, 90, 150 & 210 min of glucose administration to get postprandial glucose levels (PPG1, PPG2, PPG3 & PPG4). All other days, the animals of the groups were administered the respective extracts at fixed time of the day for 30 days. Body weight of each animal on every day, and serum samples of randomly selected animals from each group at the bigning and end of the study was checked for the serum glucose, creatine, urea, alkaline phosphatse, alkaline transaminase, cholesterol, triglycerides, high density lipoprotein (HDL), low density lipoprotein (LDL), very low density lipoprotein (VLDL) and insulin. At the end of the study 60% of the animals from each group were euthanized with an over dose of anaesthesia (Xylazine-Ketamine) and liver, kidney, pancreas were removed, fixed in 10% formalin for histopathological examination. All the grouped data were statistically evaluated with SPSS 11.0 software. Data collected were statistically analysed using non parametric statistical methods. A value of $p<0.05$ was considered to indicate statistical significance. All results are expressed as mean±standard deviation.

Figure 7A:
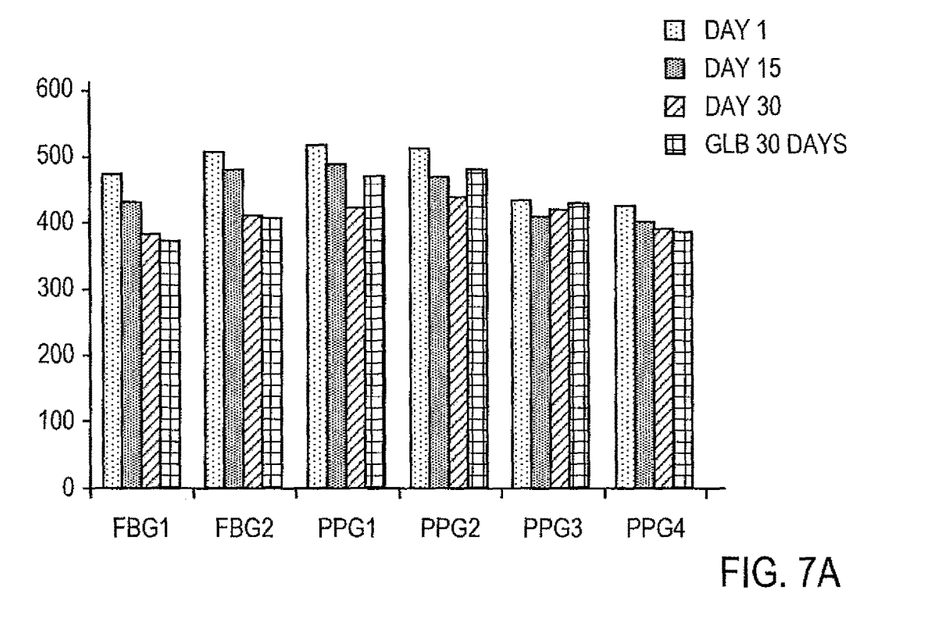
Figure 7B:
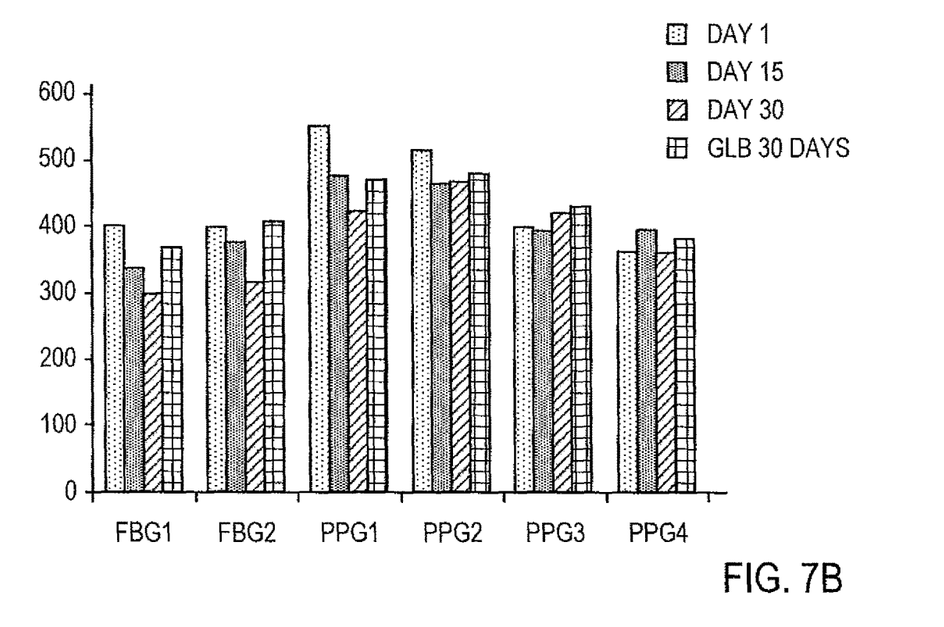
Figure 7C:
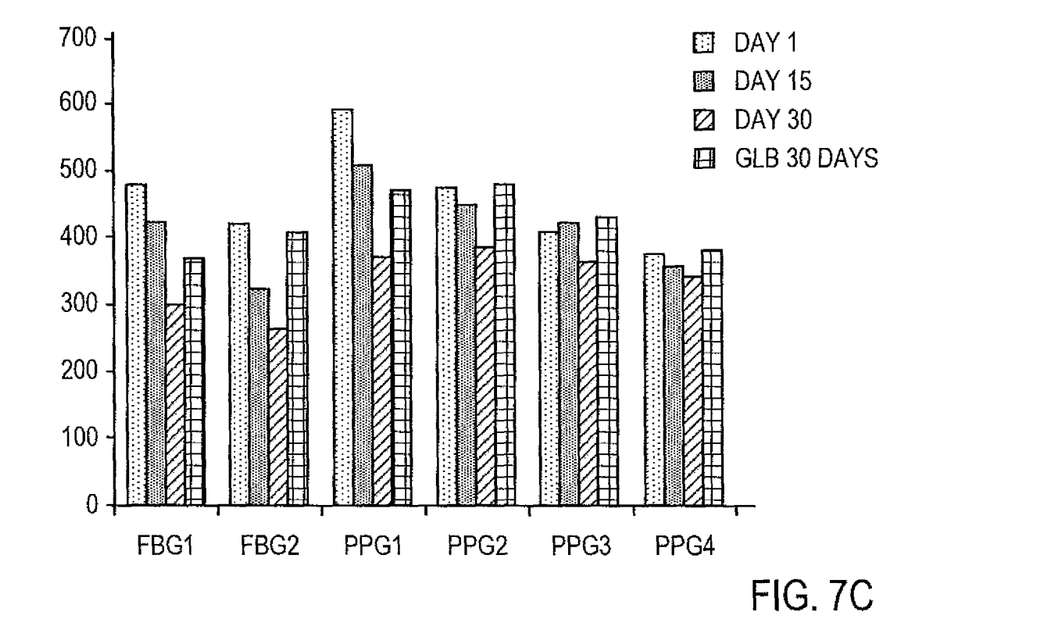

In the 30 days GTT study, polyphenol isolate containing 75% polyphenols and minimum 8% procyanidin Type A polymer and 0.5% procyanidin Type B polymer (Extract C) was found to be most effective in reducing the blood-sugar levels compared to 45% (Extract B) and 20% polyphenol isolates (Extract A), indicating a clear linear enhancement of bioactivity with polyphenol/procyanidin content. In addition, removal of coumarins and cinnmaldehyde was found to offer no change in bioactivity. Group 3 (GP3), treated with extract C, supplementation at 300 mg/Kg dosage resulted in 12.57% reduction FBG level on 15th day and 38.3% reduction on the 30th day. PPG1 level reduced to 13.4% on 15th day & 37.08% on 30th day, when compared to the initial PPG1 level. Further, magnitude of difference between FBG & PPG was minimum in GP3 (Extract C) as compared to controls GTT study in comparison with Glibenclamide on day 30, shows more pronounced effect on GP3 group (FIG. 7).

Figure 8:
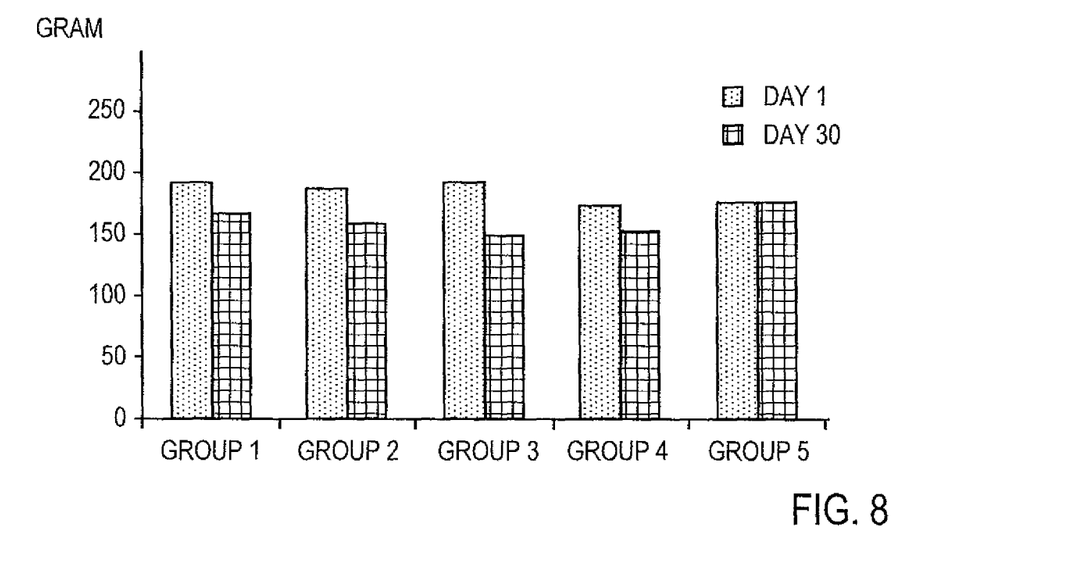
FIG. 8: Effect of extracts of 20%, 45% and 75% polyphenol content on the body weight of diabetic rats FIG. 9 (A and B): Effect of extracts of 20%, 45% and 75% Polyphenol content on the Lipid & Biochemical profile of diabetic rats.

GP3 treatment has also shown an indication of weight loss in both normal and diabetic rats after 30 days supplementation, more pronounced when compared to Glibenclamide group, statistically significant ($p<0.05$) (FIG. 8). So, it is clear that the polyphenol/procyanidin content has a direct relationship with the body weight control, irrespective of coumarin or cinnamaldehyde content.

Figure 9A:
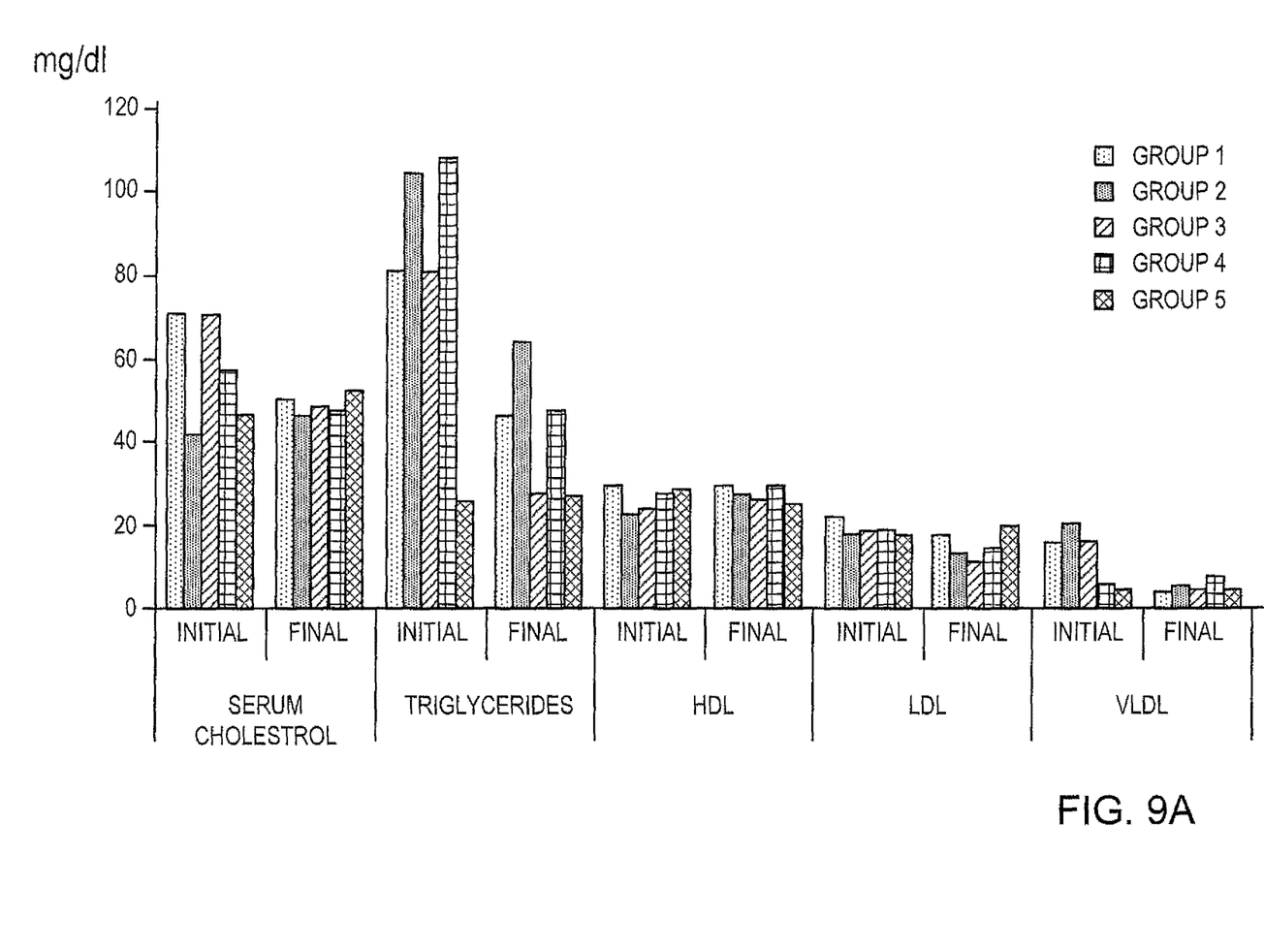
Figure 9B:
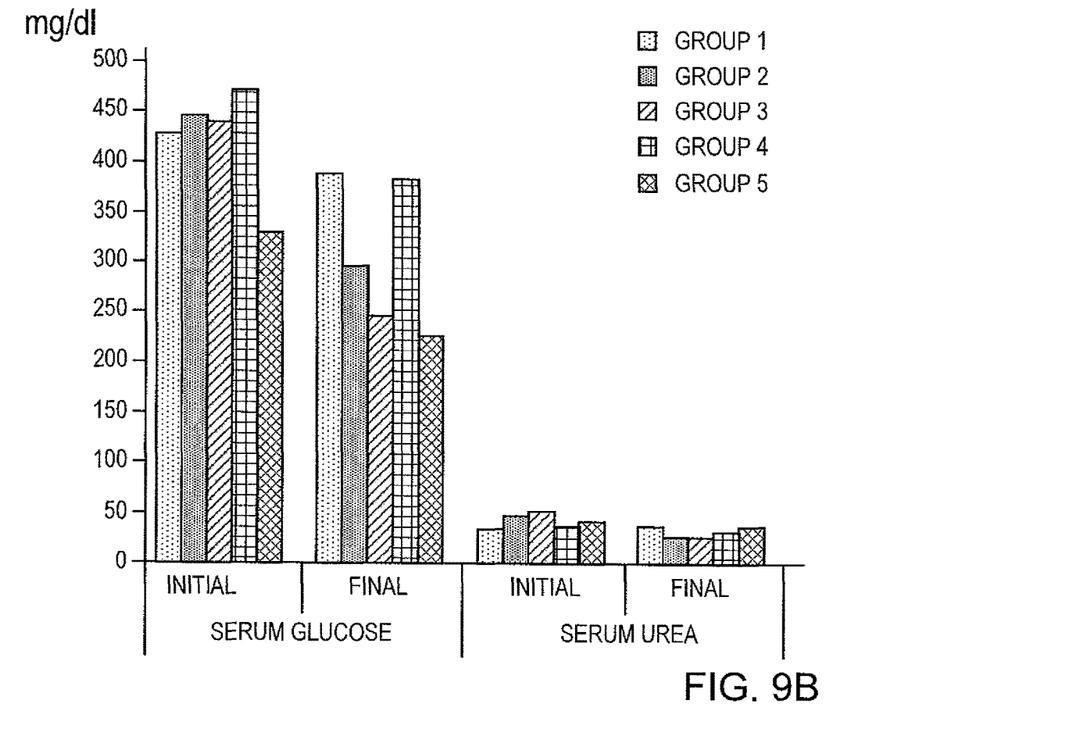

Lipid profile reflected a reduction in serum cholesterol, triglycerides, LDL & VLDL; and slight increase in HDL levels upon treatment with various polyphenol/procyanidin treatment groups, which was also more predominant in the Extract C group as compared lower grades extract groups A & B (FIG. 9). The negative control group (GPS) showed elevation in the entire lipid profile.

Figure 10:
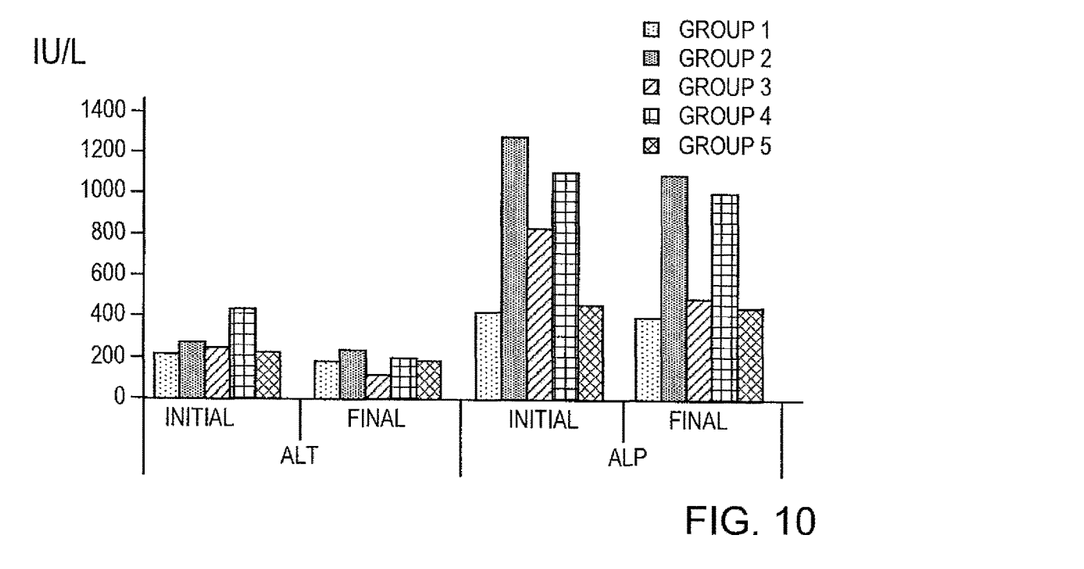
FIG. 10: Effect of extracts of 20%, 45% and 75% polyphenol content on the liver function markers of diabetic wistar albino rats

There was a reduction in serum glucose level, serum urea, and level of liver function marker enzyme ALT & ALP, upon 30 days treatment of GP3, as compared to the lower polyphenol/procyanidin groups A & B and positive control glybenclamide group (FIG. 10) and an elevation in insulin levels (1.1 μIU/ml) as compared to the GP4 (0.4 μIU/ml) (Chemiluminescence method—human specific kit was used), upon 30 days treatment. This clearly shows the effect of de-coumarinated polyphenol isolates and its effect upon liver function and pancreas. Increase in insulin levels with respect to the polyphenol content shows the insulinotropicity upon polyphenol/procyanidin content.

The invention will now be illustrated with working examples. It is to be understood that the specific example being given here are by way of illustration and are not intended to be taken restrictively to imply any limitation on the scope of the present invention.

The present invention relates to a novel method/process for selective extraction of bioactive and bioavailable cinnamon polyphenols and procyanidin oligomers both type A and type B, with more than 90% purity as Gallic acid equivalent, and containing the procyanidin A type polymers within a range of 5-20% and procyanidin B type polymers within a range of 0.5-5% as characterized by LC/MS and by eliminating the toxic coumarins, cinnamaldehyde etc to not more than 100 ppm levels, using non toxic solvents.

The process by which dried inner barks of various *cinnamomum* species, containing various levels of toxic coumarins (eg. *cinnamomum cassia*) and *cinnamomum* species which does not contain or very low content coumarins (*cinnamomum zeylanicum*) can be converted to various value added products; a free flowing dark brown liquid called oleoresin for flavor application and coumarin free polyphenol isolates with not less than 90% polyphenol content and not less than 8% procyanidin type A polymer and 0.5% type B polymer in water soluble powder form. The above said process comprises the following steps:
  a. drying cinnamon/cassia at 50 to 60° C. and coarse grinding and flaking to 1 to 25 mm pieces and extracting with a mixture of hexane and acetone, at 60 to 90% v/v of hexane and circulating for 2 hr at 20 to 50° C., in a stainless steel steam jacketed vessel with a condenser and solvent dispensing lines. Lower aliphatic hydrocarbons with 5 to 8 carbon atoms can be used instead of hexane and lower aliphatic ketones like butanone, pentanone can be employed instead of acetone. Filtering and the miscella and evaporating under reduced pressure to contain less than 25 ppm solvent residue, shall provide a free flowing dark brown liquid called oleoresin suitable for flavor application.
  b. the waste obtained after hexane/acetone extraction of oleoresin was dried under vacuum at a temperature of less than 50° C. to remove the imbibed solvent to less than 5% level without damaging the active polyphenol content in cinnamon matrix.

The extract obtained from the process is an antioxidant which finds application in nutraceutical, dietary supplement or cosmeceutical fields, as evident from the high ORAC value, minimum of 3000 μmol TE/g and increases linearly to a maximum of 7000 μmol TE/g with increase in polyphenol content from 20 to 75%.

The present invention also relates to a process for the preparation of highly stabilized water soluble polyphenol composition from various *cinnamomum* species for the best bioactivity as exemplified by the antidiabetic potential, insulinotropicity, lowering cholesterol (low density and very low density), decreasing the liver function markers like ALP and ALT and for maintaining overall health in rat study.

A linear relation between *cinnamomum* species derived polyphenol/procyanidin content and biological activity was established and found that polyphenol isolate with 75% polyphenol with 8% procyanidin A type polymer content is having three times more bioactivity than 20% polyphenol isolate containing 3% procyanidin type A polymer content.

The present invention also describes a process for the isolation of more than 90% gallic acid equivalent polyphenol content and its formulation to stable not less than 75% gallic acid equivalent polyphenol powder for delivering the maximum health benefits such as in vivo antioxidant effect, blood sugar management potential, insulin potentiating effect, body weight loosing effect, Cholesterol lowering, with a minimum of 12 years of shelf life when stored in closed containers under ambient conditions etc.

Example 1

5 Kg of dried *cinnamomum cassia* bark (polyphenol content 9.03% gallic acid equivalent and coumarin content 6.1%) is coarse ground and flaked to 1 to 25 mm pieces, and charged into a stainless steel vessel with a steam jacketing condenser and solvent dispensing lines. A mixture of hexane and acetone, containing 70% v/v of hexane, (20 Lit) is pumped into vessel and circulated for 2 hours at 45° C. The solvent is filtered and stored in a separate tank. The extraction was repeated two more times and the miscella at various stages is mixed. It is then evaporated under reduced pressure to contain less than 30 ppm solvent residues. 411.5 g of free flowing dark brown cinnamon flavour liquid (oleoresin) was obtained. The residue after extraction was dried under vacuum below 60° C. to less than 3% solvent residue level.

Example 2

900 g of above waste (polyphenol content 8.1% gallic acid equivalent) was extracted with 2.7 Lit of acetone and water, 50% v/v for 3 times at 45° C. with circulation. The miscella is filtered and evaporated under vacuum at 50° C. to 2 Lit (a total dissolved solid level of 7.5% w/v). The extract 2 Lit, is allowed to settle at 20° C. for 6 hours and filtered. The solid mass (20.9 g) thus obtained is insoluble in water and contains higher molecular weight oligomers of procyanidins. The filtrate (2 Lit) containing 115 g solids with 50.08% polyphenol content is loaded onto a column filled with adsorbant resin and washed with water at a rate of 2 column volume/h. After the washings, column is eluted with 1 column volume of ethanol. The ethanol eluent is collected, evaporated under vacuum and spray dried to get free flowing polyphenol rich powder (58.1 g powder with 91.2% gallic acid equivalent) was obtained. The product was found to contain 13.2% procyanidin type A polymers, 2.65% Type B polymers and 93 ppm coumarin. The polyphenol recovery from column was 92.4%.

25 g of polyphenol isolate thus obtained with 91.2% gallic acid equivalent, was dissolved in 150 mL of distilled water and 2.5 g of maltodextrin was added and homogenized under 250 bar pressure. It is then spray dried at inlet temperature 176° C. and outlet temperature 90° C., to get free flowing powder (76.8% gallic acid equivalent) with increased water solubility and stability towards oxidation.

Example 3

900 g of the waste in Example 1 obtained after oleoresin extraction was extracted with 5.4 Lit of ethyl alcohol and water (50% v/v) for 3 times at 45° C. with circulation. The miscella is filtered and evaporated under vacuum at 50° C. to 2.4 Lit (a total dissolved solid level of 4.5% w/v). The extract 2.5 Lit, is allowed to settle around 20° C. for 6 hours and filtered. The solid mass (9.1 g) thus obtained is insoluble in water and contains higher molecular weight oligomers of procyanidins. The filtrate (2.5 Lit) containing 116.1 g solids with 44.2% polyphenols is loaded onto a column filled with adsorbent resin and washed with water at a rate of two column volume/h. The column was also washed with 2 column volumes of hot water and then with 3 column volumes of water containing 1% ethyl alcohol. After the washings, column is eluted with 1 column volume of ethanol. The ethanol eluent is collected, evaporated under vacuum and spray dried to get free flowing polyphenol rich powder (51.5 g powder with 91.2% gallic acid equivalent) was obtained. The product was found to contain 11.6% procyanidin type A polymer, 1.91% Type B polymer and 87 ppm coumarin. The polyphenol recovery from column was 91.2%.

Example 4

900 g of the waste in Example 1 after oleoresin extraction was extracted with 9 Lit of water at 85° C. at pH 4.5 (adjusted with acetic acid) with circulation for 2 h. The extraction was repeated for 3 more times. The miscella is filtered and evaporated under vacuum at 50° C. to 3.5 Lit (a total dissolved solid level of 5% w/v). The extract 3.5 Lit, is allowed to settle at low temperature at 20° C. for 6 h and filtered. The solid mass (13.9 g) thus obtained is insoluble in water and contains higher molecular weight oligomers of procyanidins. The filtrate (3.5 Lit containing 175.6 g solids with 32.08% polyphenol content) is loaded onto a column filled with adsorbent resin and washed with water at a rate of 2 column volume/h. After the washings, column is eluted with 1 column volume of ethanol. The ethanol eluent is collected, evaporated under vacuum and spray dried to get free flowing polyphenol rich powder (46.8 g powder with 92.3% gallic acid equivalent) was obtained. The product was found to contain 10.8% procyanidin type A polymers, 1.28% Type B polymers and 165 ppm coumarin. The polyphenol recovery from column was 93.4%.

Example-5

Extraction was also performed on ground and flaked *cinnamomum cassia* bark with 70/30 v/v ethanol/water (4 times) without using hexane or acetone. Ethanol/water misella was filtered and concentrated to a brix level of 20% under vacuum at 40° C. to get water solution containing the polyphenols (22.4% gallic acid equivalent) and coumarins (6.8%). It is kept for 3 hr and filter to remove the settlings. The filtrate is mixed with 2 times the volume of ethanol and centrifuged. The clear supernated liquid thus obtained is again evaporated to remove the ethanol and passed through the adsorbent resin column as described in above examples 1 to 4 and spray dried to get free flowing powder with more than 90% gallic acid equivalent, polyphenol powder.

Example-6

All the above experiments were repeated with *Cinnamomum Zeylanicum* to prepare more than 92% gallic acid equivalent of polyphenol content and more than 8% procyanidin Type A polymer and procyanidin Type B polymer with no coumarins and less than 100 ppm of cinnamaldehyde.

Example-7

Isolated polyphenol with not less than 90% purity, eluted from column was dried to a pasty mass by evaporating the alcohol at temperature not more than 50° C., under vacuum. The paste was then added slowly to a maltodextrin solution in water and homogenized at 200 to 300 bar pressure to get a water solution. The solution is filtered and spray dried at inlet temperature 160 to 180° C. to get free flowing powder with minimum 75% gallic acid equivalent polyphenol content, not less than 8% Type A polymer and not less than 0.5% type B polymer with a coumarin and cinnmaldehyde content less than 100 ppm. The maltodextrin content can be minimum of 10% of the cinnamon extract content.

Other encapsulating agents and carriers which can be used for this purpose include, but not limited to gum arabic, gum accacia, cyclodextrin, pectins, starch, xanthum gum etc, either in combination or alone for this process.

Example 8

GTT Study on normal rats as explained above

Example 9

GTT study, Lipid profile, Liver function markers, hematological parameters measurements, histopathology of organs of diabetic rats upon 30 days supplementation of cinnamon polyphenols.

We claim:
1. A process for selective extraction of bioactive, bioavailable and stable cinnamon polyphenols and procyanidin oligomers of the type A and type B of more than 90% purity as gallic acid equivalent which comprises the steps of
   A) extracting dried and powdered bark of *cinnamomum* species with an organic solvent comprising (i) 60 to 90% v/v of at least one $C_5$-$C_6$ aliphatic hydrocarbon and (ii) at least one lower aliphatic ketone to obtain a solvent extract and a residue, said residue comprising coumarins and cinnamaldehyde;

B) filtering and evaporating the solvent extract under reduced pressure to obtain a free flowing oleoresin and waste product associated therewith;

C) drying the residue comprising coumarins and cinnamaldehyde under vacuum and extracting said dried residue with a mixture of water and acetone, or water and lower alcohol to further obtain a second extract;

D) evaporating and drying said second extract to obtain a solid mass with a total dissolved solid level of 5%-20% and further allowing said second extract to settle and further filtrating said second extract to obtain a filtrate;

E) eluting said filtrate with lower alcohols and acetone either alone or in combination with water to obtain an eluent;

F) evaporating said eluent under vacuum to obtain a free flowing polyphenol rich powder containing procyanidin type A and B polymers of less than 100 ppm of coumarins and cinnamaldehyde.

2. The process as claimed in claim 1, wherein procyanidin A type polymers is within the range of 5-20% and procyanidin B type polymers is within the range of 0.5-5% coumarins and cinnamaldehyde not more than 100 ppm levels.

3. The process as claimed in claim 1, wherein said extracting with organic solvents is carried out by circulating a mixture of hexane and acetone at 60-90% v/v of hexane.

4. The process as claimed in claim 1, wherein said waste product associated with said free flowing oleoresin is dried under vacuum at a temperature below 50° C. to remove imbibed solvents to less than 5% level.

5. The process as claimed in claim 4, wherein said waste product associated with said free flowing oleoresin is additionally extracted with acetone and water or ethanol and water at 30% to 60% v/v of the organic solvent for 3 hours at less than 50° C.

6. A stable composition having a minimum of 12 months shelf life for blood sugar management cholesterol lowering and antioxidant effect comprising cinnamon polyphenol rich powder having not less than 75% gallic acid equivalent and not less than 8% procyanidin type A polymer and not less than 0.5% type B polymer, obtained by a process as claimed in claim 1 and a pharmaceutically acceptable carrier or diluent.

7. The composition as claimed in claim 6, comprising not less than 45% polyphenol content as gallic acid equivalent and not less than 5% procyanidin Type A polymer and 0.5% Type B polymer.

8. A flavour composition comprising free flowing oleoresin obtained by organic solvent extraction and evaporation of barks of *cinnamomum* species as claimed in claim 1.

9. Neutraceuticals and pharmaceutical composition containing a composition as claimed in claim 6.

10. A stable composition having a minimum of 12 months shelf life for blood sugar management cholesterol lowering and antioxidant effect comprising cinnamon polyphenol rich powder having not less than 75% gallic acid equivalent and not less than 8% procyanidin type A polymer and not less than 0.5% type B polymer, obtained by a process as claimed in claim 2 and a pharmaceutically acceptable carrier or diluent.

11. A stable composition having a minimum of 12 months shelf life for blood sugar management cholesterol lowering and antioxidant effect comprising cinnamon polyphenol rich powder having not less than 75% gallic acid equivalent and not less than 8% procyanidin type A polymer and not less than 0.5% type B polymer, obtained by a process as claimed in claim 3 and a pharmaceutically acceptable carrier or diluent.

12. A stable composition having a minimum of 12 months shelf life for blood sugar management cholesterol lowering and antioxidant effect comprising cinnamon polyphenol rich powder having not less than 75% gallic acid equivalent and not less than 8% procyanidin type A polymer and not less than 0.5% type B polymer, obtained by a process as claimed in claim 4 and a pharmaceutically acceptable carrier or diluent.

13. A stable composition having a minimum of 12 months shelf life for blood sugar management cholesterol lowering and antioxidant effect comprising cinnamon polyphenol rich powder having not less than 75% gallic acid equivalent and not less than 8% procyanidin type A polymer and not less than 0.5% type B polymer, obtained by a process as claimed in claim 5 and a pharmaceutically acceptable carrier or diluent.

14. The composition as claimed in claim 10, wherein it comprises not less than 45% polyphenol content as gallic acid equivalent and not less than 5% procyanidin Type A polymer and 0.5% Type B polymer.

15. The composition as claimed in claim 11, wherein it comprises not less than 45% polyphenol content as gallic acid equivalent and not less than 5% procyanidin Type A polymer and 0.5% Type B polymer.

16. The composition as claimed in claim 12, wherein it comprises not less than 45% polyphenol content as gallic acid equivalent and not less than 5% procyanidin Type A polymer and 0.5% Type B polymer.

17. The composition as claimed in claim 13, wherein it comprises not less than 45% polyphenol content as gallic acid equivalent and not less than 5% procyanidin Type A polymer and 0.5% Type B polymer.

18. Neutraceuticals and pharmaceutical composition containing compositions as claimed in claim 10.

19. Neutraceuticals and pharmaceutical composition containing compositions as claimed in claim 11.

20. Neutraceuticals and pharmaceutical composition containing compositions as claimed in claim 12.

21. Neutraceuticals and pharmaceutical composition containing compositions as claimed in claim 13.

22. A method for reducing blood sugar and cholesterol levels and weight controlling in mammals comprising the steps of administering an effective dosage of cinnamon procyanidine of type A and B obtained by a process as claimed in claim 1.

* * * * *